US010682186B2

(12) United States Patent
Saur et al.

(10) Patent No.: US 10,682,186 B2
(45) Date of Patent: Jun. 16, 2020

(54) VISUALIZATION SYSTEM HAVING AN ILLUMINATION APPARATUS

(71) Applicant: Carl Zeiss Meditec AG, Jena (DE)

(72) Inventors: Stefan Saur, Aalen (DE); Marco Wilzbach, Aalen (DE); Christopher Kaesbach, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 16/139,033

(22) Filed: Sep. 22, 2018

(65) Prior Publication Data
US 2019/0090958 A1 Mar. 28, 2019

(30) Foreign Application Priority Data
Sep. 22, 2017 (DE) .......................... 10 2017 216 852

(51) Int. Cl.
*A61B 34/20* (2016.01)
*A61B 90/20* (2016.01)
*A61B 90/30* (2016.01)
*A61B 90/35* (2016.01)
*A61B 90/00* (2016.01)
(Continued)

(52) U.S. Cl.
CPC .............. *A61B 34/20* (2016.02); *A61B 90/20* (2016.02); *A61B 90/30* (2016.02); *A61B 90/35* (2016.02); *A61B 90/361* (2016.02); *G02B 21/0012* (2013.01); *G02B 21/06* (2013.01); *G06T 7/70* (2017.01); *A61B 90/25* (2016.02); *A61B 2034/2051* (2016.02); *A61B 2034/2055* (2016.02); *A61B 2034/2057* (2016.02); *A61B 2090/309* (2016.02); *A61B 2090/371* (2016.02); *A61B 2090/372* (2016.02); *A61B 2090/502* (2016.02); *G06T 2207/30244* (2013.01); *H04N 5/2256* (2013.01)

(58) Field of Classification Search
CPC ....... G01N 21/8806; G01N 2021/8838; H04N 5/2354
See application file for complete search history.

(56) References Cited

U.S. PATENT DOCUMENTS 6,430,433 B1  8/2002 Luber et al.
2007/0265495 A1* 11/2007 Vayser .................. A61B 1/045
600/109

OTHER PUBLICATIONS

Office Action issued in German Patent Application No. DE 10 2017 216 852.8 (from which this application claims priority), dated May 2, 2018 and English language machine translation thereof.

\* cited by examiner

Primary Examiner — James M Pontius
(74) Attorney, Agent, or Firm — Falk Ewers; Ewers IP Law PLLC

(57) ABSTRACT

A visualization system includes an image capturing apparatus configured to observe an object region having an object plane, an illumination apparatus that is mechanically decoupled from the image capturing apparatus, having an actuator for controlling at least one property of the illumination apparatus, a control unit connected to the actuator, and a pose capturing unit connected to the control unit. The pose capturing unit is embodied so that a relative pose between the illumination apparatus and the image capturing apparatus is ascertainable, wherein the actuator is actuable by the control unit, in dependence on the relative pose ascertained by the pose capturing unit, in a manner such that the at least one property of the illumination apparatus is settable such that the object region having the object plane is illuminated by the illumination apparatus.

11 Claims, 3 Drawing Sheets

(51) Int. Cl.
*G06T 7/70* (2017.01)
*G02B 21/00* (2006.01)
*G02B 21/06* (2006.01)
*A61B 90/50* (2016.01)
*A61B 90/25* (2016.01)
*H04N 5/225* (2006.01)

VISUALIZATION SYSTEM HAVING AN ILLUMINATION APPARATUS

CROSS REFERENCE TO RELATED APPLICATIONS

This application claims priority to German patent application DE 10 2017 216 852.6, filed Sep. 22, 2017, the entire content of which is incorporated herein by reference.

TECHNICAL FIELD

The invention relates to a visualization system having an illumination apparatus.

BACKGROUND

In medical technology, optical visualization apparatuses are used during surgery. One known visualization apparatus is an optical surgical microscope comprising an observation optical unit and eyepieces for observing an object region and an illumination apparatus for illuminating said object region. The object region is a surgical site. Surgical microscopes can be additionally or alternatively equipped with an image capturing apparatus, for example one or more cameras. The image recorded by the image capturing apparatus is displayed on a display apparatus, for example on a screen.

The image capturing apparatus and the illumination apparatus are mechanically coupled, that is to say mechanically connected in such a way that during a position or pose change of the surgical microscope, the image capturing apparatus and the illumination apparatus are moved together. In this way, illumination of the object region recorded by the image capturing apparatus, the surgical site, is ensured at every positional and angular setting.

However, mechanical coupling between the illumination apparatus and the image capturing apparatus can no longer be assumed in future systems. Image capturing apparatus and illumination apparatus can form systems that are independent of one another and that are arranged at different holders or stands.

Optimum lighting of a surgical site, however, is essential during surgical interventions. For the observer and surgeon, optimum lighting of the region to be operated on is a prerequisite for good visualization in order to be able to see extremely fine tissue structures. Incorrectly set illumination can cause tissue damage in a patient due to overheating.

SUMMARY

It is an object of the invention to provide a visualization system having a mechanically decoupled illumination apparatus, by way of which the illumination of an object region is improved.

The object is achieved by a visualization system as disclosed herein.

According to an aspect of the invention, the visualization system comprises an image capturing apparatus for observing an object region having an object plane, an illumination apparatus that is mechanically decoupled from the image capturing apparatus, having an actuator for controlling at least one property of the illumination apparatus, a control unit connected to the actuator, and a pose capturing unit connected to the control unit.

The pose capturing unit is configured to ascertain a relative pose between the illumination apparatus and the image capturing apparatus, wherein the actuator is actuable by the control unit, in dependence on the relative pose which has been ascertained by the pose capturing unit, in a manner such that the at least one property of the illumination apparatus is settable such that the object region having the object plane is illuminated by the illumination apparatus.

The visualization system comprises an image capturing apparatus for observing an object region and an illumination apparatus which is mechanically decoupled from the image capturing apparatus.

The image capturing apparatus is part of the visualization system for observing a three-dimensional object region having an object plane. The object region is a surgical region. A surgical region is a tissue region that is to be examined or operated on, and is also referred to as a surgical site. A tissue region in this context can comprise cell tissue, bone and/or artificial body elements. The geometric relationships in the three-dimensional object region are dependent on the tissue to be examined. In order to uniquely describe the geometric properties for the image capturing apparatus and the illumination apparatus in the object region, they are referred to as the object plane. The object plane is an observation plane in the object region.

The optical unit of the image capturing apparatus defines a focal plane. In an optical or digital surgical microscope, the focal plane is a plane in an axial position along the optical axis of the observation beam path, in which the focus of the imaging attains a maximum. The optical unit of the image capturing apparatus can also sharply image above and below the focal plane a region which is defined by the depth of field. For example, if the image capturing apparatus is a surgical microscope, the focal plane and the object plane are situated in the same plane.

The image capturing apparatus is configured to reproduce the object region in magnified fashion or present it without magnification. A magnification factor can be dependent on the type of the tissue region to be operated on.

The image capturing apparatus can be formed by at least one camera or an image sensor, for example a charge-coupled device (CCD) sensor. The image capturing apparatus can comprise optics elements, for example lens elements, filters and/or stops. The optics elements can form a magnification optical unit. The image capturing apparatus can capture an individual image or a video sequence. The image capturing apparatus can be embodied to capture 2D images and/or 3D images. The visualization system can include a display apparatus which presents the image that has been recorded by the image capturing apparatus.

The illumination apparatus can comprise a xenon or halogen light source or be formed by an LED unit. One or more optics elements that focus the light or transfer it into a parallel beam path can be arranged in front of the light source. The illumination apparatus can comprise one or more filters for providing illumination light in a specific wavelength range and/or with a desired brightness. The illumination apparatus can include stops for setting an illumination spot size in the object plane that is to be illuminated.

The illumination apparatus is mechanically decoupled from the image capturing apparatus. This means that no mechanical connection, no fixed mechanical cohesion, exists between the illumination apparatus of the image capturing apparatus. A position or pose of the illumination apparatus can be changed without changing the position or pose of the image capturing apparatus in the process. Both apparatuses are mechanically independent appliances. The illumination apparatus and the image capturing apparatus can be arranged in space independently from one another.

For this purpose, the illumination apparatus and the image capturing apparatus can be attached to different stands or holding arms. The orientation and position of an illumination beam path relative to the object region is variable independently of the orientation and position of an observation beam path. By contrast, the illumination beam path and the observation beam path in a classical surgical microscope are guided through a common main objective and are in this way mechanically and even optically coupled.

The illumination apparatus comprises an actuator for controlling the at least one property of the illumination apparatus. A property is understood to mean a mechanical, optical or electrical property or function of the illumination apparatus. The actuator converts the control signals into a mechanical movement or into an optical or electrical property. The actuator can include an individual actuator element or an entire actuator assembly. In the case of conversion into a mechanical movement, the actuator comprises a drive element. The drive element can position the illumination apparatus for example in space or set an angle change to effect orientation. The drive element can also move an optics element or swivel a stop in or out in order to set an illumination zoom or a spot size in the object plane. The actuator can comprise an individual drive element or an assembly having a plurality of drive elements. A drive element can be a motor, such as a servo motor or a stepper motor.

The actuator can also be configured to set an optical function of the illumination apparatus. To this end, the actuator can be, for example, an LCD matrix in order to set the brightness or spot size in the object plane. The actuator can also be an electrical assembly, which sets an electrical property of the light source and provides, for example, current having a specific pulse frequency or pulse width to set the intensity of the light source. The actuator can also be used to effect a plurality of properties together. For example, a mechanical drive element can insert a filter into the beam path and consequently set an optical property, the wavelength range of the illumination light. The illumination apparatus can comprise a plurality of actuators to actively set a plurality of properties of the illumination apparatus.

A control unit is connected to the actuator. The control unit is likewise connected to the pose capturing unit. These connections can be effected via a cable, for example via a network or coaxial cable, or without a cable, for example via infrared, radio, Bluetooth or WLAN. The control unit comprises a computation unit and a memory and can include further electronics assemblies. The control unit can be connected to a screen and provide one or more interfaces. The control unit can process the data that have been ascertained by the pose capturing unit and calculate therefrom control signals for the at least one actuator of the illumination apparatus.

The pose capturing unit is configured to ascertain a relative pose between the illumination apparatus and the image capturing apparatus. The relative pose is defined as a relative position and orientation of the illumination apparatus and the image capturing apparatus with respect to one another. The relative position defines a translation in the direction of an x-axis, a y-axis, and a z-axis of an orthogonal coordinate system. The relative orientation defines a rotation about the x-axis, the y-axis, and the z-axis. This also comprises other coordinate systems or equivalent coordinate system representations that describe the space in a different way.

The pose capturing unit can be formed by a computational unit which evaluates the images which have been recorded by the image capturing apparatus and ascertains therefrom a relative pose between the image capturing apparatus and the illumination apparatus. The actuator is actuable by the control unit in dependence on the ascertained relative pose in a manner such that a property of the illumination apparatus is set such that the object region having the object plane is illuminated by the illumination apparatus. This property can be, for example, a position, orientation or illumination spot size in the object plane.

The pose capturing unit can alternatively also be a known tracking system which ascertains the relative pose between the illumination apparatus and the image capturing apparatus using markers which are arranged on said two apparatuses. Tracking systems can operate on the basis of infrared light or white light. Electromagnetic tracking systems are also known. Also available are tracking systems without markers, which can ascertain a relative pose between the illumination apparatus and the image capturing apparatus by image evaluation of camera image data.

The image capturing apparatus is an optomechanical system, for example a digital surgical microscope having at least one camera. The image capturing apparatus comprises optics elements having optical properties that define a focal plane. The spatial assignment and the relative pose between the image capturing apparatus and the focal plane are uniquely specified in this way.

If the object region having the object plane is positioned in the focal plane, the object plane coincides with the focal plane. If the pose and the orientation of the image capturing apparatus are known because they have been ascertained by way of the pose capturing unit, the position and orientation of the object plane can be uniquely derived therefrom.

The control unit, which processes the data of the pose capturing unit, can calculate therefrom a control signal for the actuator of the illumination apparatus. The relative pose between object plane, image capturing apparatus and illumination apparatus, which in this way form a triangular arrangement in space, is ascertainable. For this reason, the control apparatus can calculate therefrom the necessary control signals for the actuator and actuate the latter in a manner such that the object plane and consequently the object region are illuminated.

In one exemplary embodiment of the invention, the pose capturing unit is configured to permit a relative pose between the image capturing apparatus and the object plane to be ascertainable.

The image capturing apparatus can also be part of a visualization system which is borne on the head. One example of a visualization system that can be borne on the head is a head-mounted display, also referred to as a HMD. The HMD comprises a display, which is arranged in front of the eyes and presents an image of the object region which has been recorded by the image capturing apparatus. The object region can be observed with or without magnification. A magnification factor can also be very low, for example less than two. One or more optics elements can also be arranged on the HMD between the eye of the observer and the object region.

A head-borne visualization system is not rigid. The observer may intentionally or unintentionally perform small movements, even trembling movements are possible.

For this reason it is typical for the pose capturing unit to be configured to permit a relative pose between the image capturing apparatus and the object plane to be additionally ascertainable. The control unit, which processes the data of the pose capturing unit, can calculate a control signal for the actuator of the illumination apparatus from the relative positions and orientations between object plane, image capturing apparatus and illumination apparatus. The actuator sets the illumination apparatus in a manner such that the object plane and consequently the object region are illuminated.

In one exemplary embodiment of the invention, a property of the illumination apparatus is the orientation of the illumination apparatus toward the object plane of the object region.

The optical axis of the illumination beam path is oriented and a central point on the object plane. An orientation is attainable by way of a translational position change of the illumination apparatus in space and/or a rotational adaptation of the illumination angle. The actuator can be an individual drive element or comprise a relatively large drive unit and include, for example, one or more motors in order to convert the control signals into a mechanical movement. The actuator can set the position and/or the illumination angle in one, two or three axes to the object plane and consequently to the object region.

In one exemplary embodiment of the invention, a property of the illumination apparatus is formed from an illumination spot size, an intensity, a focus, and a zoom referred to the object plane.

The setting of one or more of said optical parameters can effect optimum lighting of the object plane and of the object region.

In one exemplary embodiment of the invention, a property of the illumination apparatus is the illumination spot size in the object plane.

The illumination spot size defines the size of the illuminated area in the object plane. If the illumination light has the shape of a cone, a circular or elliptical region in the object region is illuminated. The illumination spot forms in the object plane a settable circle when the optical axis of the illumination light cone forms a normal of the object plane.

In one exemplary embodiment of the invention, a property of the illumination apparatus is the intensity of the illumination light in the object plane.

The intensity defines the radiant power of the illumination light in the object plane. The intensity of the illumination light is perceived by the observer by way of the brightness of the illumination. If the illumination is too bright, it may dazzle, while illumination which is too weak can be perceived as inadequate. The intensity of the illumination light also determines the probability of tissue damage.

In one exemplary embodiment of the invention, a property is the focus of the illumination light in the object plane.

The focus is the focal point of the emitted illumination light. Adapting the focus effects a change in the size of the illuminated area in the object plane.

In one exemplary embodiment of the invention, a property of the illumination apparatus is the zoom setting referred to the object plane.

By adapting the illumination zoom, the size of the illuminated area in the object plane is typically settable. An illumination zoom of the illumination apparatus can be set easily and cost-effectively by way of a motor.

In one exemplary embodiment of the invention, a property of the illumination apparatus is the setting of a wavelength range.

The illumination of the object region with a specified illumination wavelength permits the visualization of specific structures. The wavelength range can be, for example, the excitation wavelength range for a fluorescence observation.

In one exemplary embodiment of the invention, the actuator is a robotic apparatus.

A robotically controlled apparatus can set a position and orientation of the illumination apparatus to the object region having the object plane. The robotically controlled apparatus can position the illumination apparatus in space and to this end move it in a translational fashion. In addition, a rotational orientation in one or more axes is possible. Robotic apparatuses can permit a movement with respect to all six degrees of freedom, in three translational axes and three rotational axes.

An illumination apparatus can thus be positioned at a free location in space that does not impair one or more observers in the performance of diagnostic or surgical work. If the surgical site is for example a narrow and deep channel, the illumination apparatus can be positioned in a direct extension of the operating channel and be oriented exactly toward the operating channel.

In one exemplary embodiment of the invention, the relative pose is ascertainable by evaluating the image data which have been recorded by the image capturing apparatus.

This is a cost-effective solution, since the relative pose between illumination apparatus and image capturing apparatus is ascertainable by software. No additional apparatuses are necessary.

In one exemplary embodiment of the invention, the pose capturing unit comprises a tracking system.

Tracking systems can be used in combination with a visualization system during surgeries. As a result, a tracking system can form a pose capturing unit which can ascertain the relative pose between the illumination apparatus and the image capturing apparatus with a high degree of accuracy.

In one exemplary embodiment of the invention, a position and orientation of the object region having the object plane are ascertainable by way of the tracking system.

A position and orientation of the object region that is to be examined and has the object plane are ascertainable by way of the tracking system. A relative pose between the object plane and the illumination device can thus advantageously be calculated. Additionally or alternatively, a relative pose between an image capturing apparatus and the object plane is ascertainable. This is advantageous if the position of the image capturing apparatus in space is changed, for example because it is arranged on the head of an observer.

In one exemplary embodiment of the invention, a light source of the illumination apparatus is controllable in dependence on the data that have been ascertained by the pose capturing unit.

The light source of the illumination device can be actuated by the control unit. The light source is typically able to be dimmed or switched off thereby, depending on the data that have been ascertained by the pose capturing unit. If it has been ascertained by the pose capturing unit that the image capturing apparatus is not directed at the object plane, the intensity of the illumination light can be reduced or the light source can be switched off.

In one exemplary embodiment of the invention, the visualization system comprises at least one further image capturing apparatus.

The visualization system can optionally also be extended for at least one second observer.

In one exemplary embodiment of the invention, the visualization system comprises at least one additional illumination apparatus having an additional actuator which is actuable by the control unit.

Two illumination apparatuses with different properties can optionally be used. For example, a first illumination apparatus can be set for producing an illumination spot for a narrow channel in the tissue region. A second illumination apparatus can be set for general illumination of the tissue region.

BRIEF DESCRIPTION OF THE DRAWINGS

The invention will now be described with reference to the drawings wherein.

DESCRIPTION OF EXEMPLARY EMBODIMENTS

Figure 1:
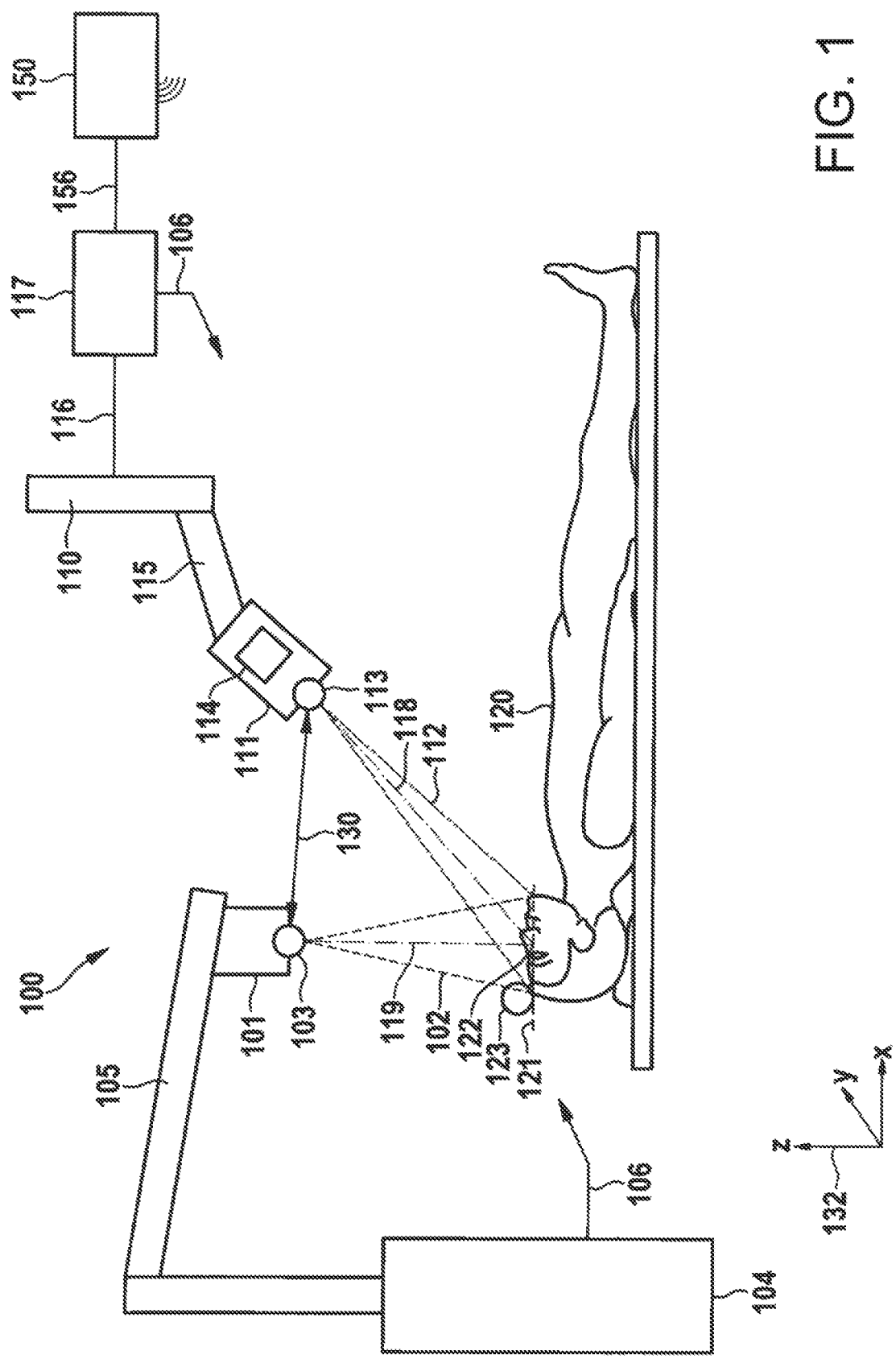
FIG. 1 shows a schematic illustration of a first visualization system.

FIG. 1 shows a schematic illustration of a first visualization system.

A first visualization system 100 comprises an observation unit 104, an illumination unit 110, and a pose capturing unit 150. The observation unit 104 has a first image capturing apparatus 101, which is arranged on a first holding arm 105. The observation unit 104 can comprise a stand and have further holding arms. The illumination unit 110 comprises an illumination apparatus 111, which is attached to a second holding arm 115.

The first image capturing apparatus 101 is directed at an object 120 that is to be observed and includes a tissue region to be examined. The object 120 that is to be observed is a patient. The body part that is to be examined is the head of the patient. The tissue region that is to be examined forms the object region and comprises an object plane 121, toward which the first image capturing apparatus 101 is oriented. The optical unit of the image capturing apparatus 101 defines a first observation beam path 102 having a first optical axis 119 and a focal plane. The focal plane of the first image capturing apparatus 101 is congruent with the object plane 121.

The first image capturing apparatus 101 can comprise a camera or an image sensor, for example a CCD chip, and be configured to record monochromatic, colored or fluorescence images. It is possible for one or more optics elements (not illustrated), for example lens elements, stops or filters, to be arranged in front of the camera or the image sensor. The first image capturing apparatus 101 can comprise an individual image sensor or a plurality of image sensors or cameras and be embodied to record 2D or 3D images.

The illumination apparatus 111 comprises a light source and an illumination optical unit.

The light source can be formed by an incandescent lamp, a halogen lamp, a xenon lamp or by an LED light source. The illumination apparatus 111 can comprise an illumination optical unit, stops and/or filters. The illumination apparatus 111 can be equipped with an illumination zoom.

The illumination apparatus 111 comprises an actuator 114, which can control a first property of the illumination apparatus 111. The actuator 114 comprises a drive element or a drive element assembly for orienting the illumination apparatus toward the object plane 121 of the tissue region that is to be examined. To this end, the orientation of the illumination apparatus 111 is rotationally settable by the actuator 114 in at least one axis, typically in two axes, of an orthogonal coordinate system 132.

In a development, the actuator 114 can be configured to move the illumination apparatus 111, which is arranged on the second holding arm 115, in translational fashion in up to three axes of the orthogonal coordinate system 132 and/or pivot it in rotational fashion about said three axes.

The observation unit 104 is connected to a control unit 117 by a first connection 106. The illumination unit 110 is connected to the control unit 117 by a second connection 116. The pose capturing unit 150 is connected to the control unit 117 by a third connection 156. The first connection 106, the second connection 116, and the third connection 117 can be embodied in cable-bound fashion via in each case one line, for example a network, a bus system, a data cable or a coaxial cable, or without cables, for example via infrared, radio, Bluetooth or WLAN.

The first image capturing apparatus 101 is a digital surgical microscope or a digital camera. The tissue region that is to be examined comprises the object plane 121 and is recorded by the first image capturing apparatus 101. The first image capturing apparatus 101 comprises a magnification optical unit and an image sensor. The image recorded by the image sensor is presented on a display apparatus (not illustrated) and shows a magnified presentation of the tissue region. A display apparatus can be a screen or a head-borne presentation apparatus.

The relative pose, i.e., the relative position and orientation between the first image capturing apparatus 101 and the illumination apparatus 111, is ascertained by the pose capturing unit 150. To this end, the first image capturing apparatus 101 comprises a first reference element 103 and the illumination apparatus 111 comprises a second reference element 113. The first reference element 103 and the second reference element 113 form reference elements for capturing position and pose. The first reference element 103 and the second reference element 113 are configured to permit a position in space referred to as an x-axis, a y-axis, and a z-axis of the orthogonal coordinate system 132 and a rotational orientation around the x-axis, the y-axis, and the z-axis of the orthogonal coordinate system 132 to be ascertainable.

If the position and orientation of the first reference element 103 and of the second reference element 113 have been ascertained by the pose capturing unit 150, the control unit 117 can calculate from said data a first reference point for the first reference element 103 and a second reference point for the second reference element 113. Between the first reference point and the second reference point, the distance and the relative position between the first image capturing apparatus 101 and the illumination apparatus 111 can be calculated. In addition, the rotational orientation around the x-axis, the y-axis, and the z-axis, referred to the orthogonal coordinate system 132, is also known due to the orientation of the first reference element 103 and the second reference element 113. Consequently, is possible to ascertain from said data a first relative pose 130, i.e., the relative position and orientation with respect to one another between the illumination apparatus 111 and the first image capturing apparatus 101.

The object plane 121 is congruent with the focal plane which is defined by the optical unit of the first image capturing apparatus 101. Since the position and orientation of the first image capturing apparatus 101 have been ascertained, the position and orientation of the focal plane are also known. The object plane 121 and the focal plane are situated in the same plane. A third reference point 122 is definable in the object plane 121. The third reference point 122 can be a point that is defined by the observation apparatus 101 and can be situated for example on the first optical axis 119 of the first observation beam path 102. Alternatively, the third reference point 122 can also be established by the observer and mark for example a distinctive structure in the tissue region.

The first reference point, the second reference point and the third reference point 122 form a triangle in space. For this reason, it is possible to calculate in the control unit 117 a target position for the illumination apparatus 111, for which an illumination beam path 112 is optimally oriented toward the object plane 121 to be illuminated.

One possibility is to orient the optical axis 118 of the illumination beam path 112 toward the third reference point 122 on the object plane 121. An orientation is attainable by way of a translational position change of the illumination apparatus 111 in space and/or a rotational adaptation of the illumination angle. The actuator 114 can be an individual drive element or comprise a relatively large drive unit and include, for example, one or more motors in order to convert the control signals into a mechanical movement. The actuator 114 can set the position and/or the illumination angle in one, two or three axes and set the illumination beam path 112 to the object plane 121 and consequently to the object region. The illumination beam path 212 can be set optimally for example when the observer can see the object region without noticeable shadows.

In a further exemplary embodiment, an optical or electrical property of the illumination apparatus 111 can be set by the actuator 114, for example the illumination spot size, a zoom setting, the light intensity, the illumination focus or the wavelength range.

The actuator 114 can also comprise a plurality of assemblies in order to set a plurality of properties. For example, a mechanical assembly can set the position and/or the orientation of the illumination angle, while a different assembly adapts the illumination spot diameter.

The illumination spot diameter in the object plane 121 can additionally also be ascertained on the basis of further properties or parameters of the first image capturing apparatus 101, for example focal distance, zoom setting or field of view. The 3D topography of the tissue region can optionally be determined by an evaluation of the image data which have been recorded by the first image capturing apparatus in order to set the illumination apparatus 111 on the basis of an ascertained 3D profile. The coordinates of the 3D topography can also be transferred by the control unit 117 to the coordinate system 132, with the result that an optimum setting of the illumination properties is attainable from those coordinates which have been ascertained by the pose capturing unit 150 and the 3D topography data. This comprises one or more of the above-mentioned properties of the illumination apparatus 111, for example position, orientation, illumination spot, zoom, focus, illumination intensity, illumination wavelength and/or illumination shape, which is settable via a stop.

The illuminated area in the object plane 121 can be circular or elliptical. It is also conceivable for the illuminated area to have any desired contour, for example if a non-symmetric stop is arranged in the illumination beam path or the stop is formed by an LCD stop which is actuable in point-wise fashion.

In another exemplary embodiment, the illuminated region can also be recorded by the first image capturing apparatus 101 and be evaluated by the control unit 117. These data can be used to supplement the data which have been provided by the pose capturing unit 150 for controlling the actuator 114. In a further implementation, it is also conceivable for the data of the illuminated region to be used as an alternative to the data which have been used by the pose capturing unit 150 for controlling the actuator 114. For this purpose, the observation unit 104 can transmit to the actuator 114 of the illumination apparatus 111, on the basis of the images which are provided by the first image capturing apparatus 101, a desired illumination shape and/or a relative pose to be set between illumination apparatus 111 and the first image capturing apparatus 101. This implementation is in particular conceivable if only a few properties, e.g., the illumination spot size and/or the illumination intensity, are intended to be controlled.

In the case of a change in the positioning of the first image capturing apparatus 101, a new relative pose between the illumination apparatus 111 and the image capturing apparatus 101 is ascertained by the pose capturing unit 150. The control unit 117 controls the actuator 114 such that the illumination apparatus 111 is once again oriented toward the object region having the object plane 221.

If the data that have been ascertained by the pose capturing unit 150 show that the first image capturing apparatus 101 is no longer oriented toward the tissue region having the object plane 121, the intensity of the illumination light can be reduced by the control unit 117, for example by dimming or switching off the light source.

In a further exemplary embodiment, a third reference element 123 can be additionally arranged on the object 120 that is to be observed. The third reference element 123 permits the determination of a position and orientation of the object 120 to be observed in space. This can be advantageous if the object 120 that is to be observed and the object plane 121 are arranged at an angle in space and/or the position of the first image capturing apparatus 101 is changed during the observation.

In yet another exemplary embodiment, the observation unit 104 can also form a hybrid system, a mixture of a conventional optical surgical microscope, which comprises a main objective and a magnification optical unit, and a digital surgical microscope.

In one exemplary embodiment of the invention, the control unit 117 can be integrated in the observation unit 104 or in the illumination unit 110. It is also conceivable that the control unit 117 is part of the pose capturing unit 150. The control unit 117 can also be formed by a separate data processing unit or a standard PC.

Figure 2:
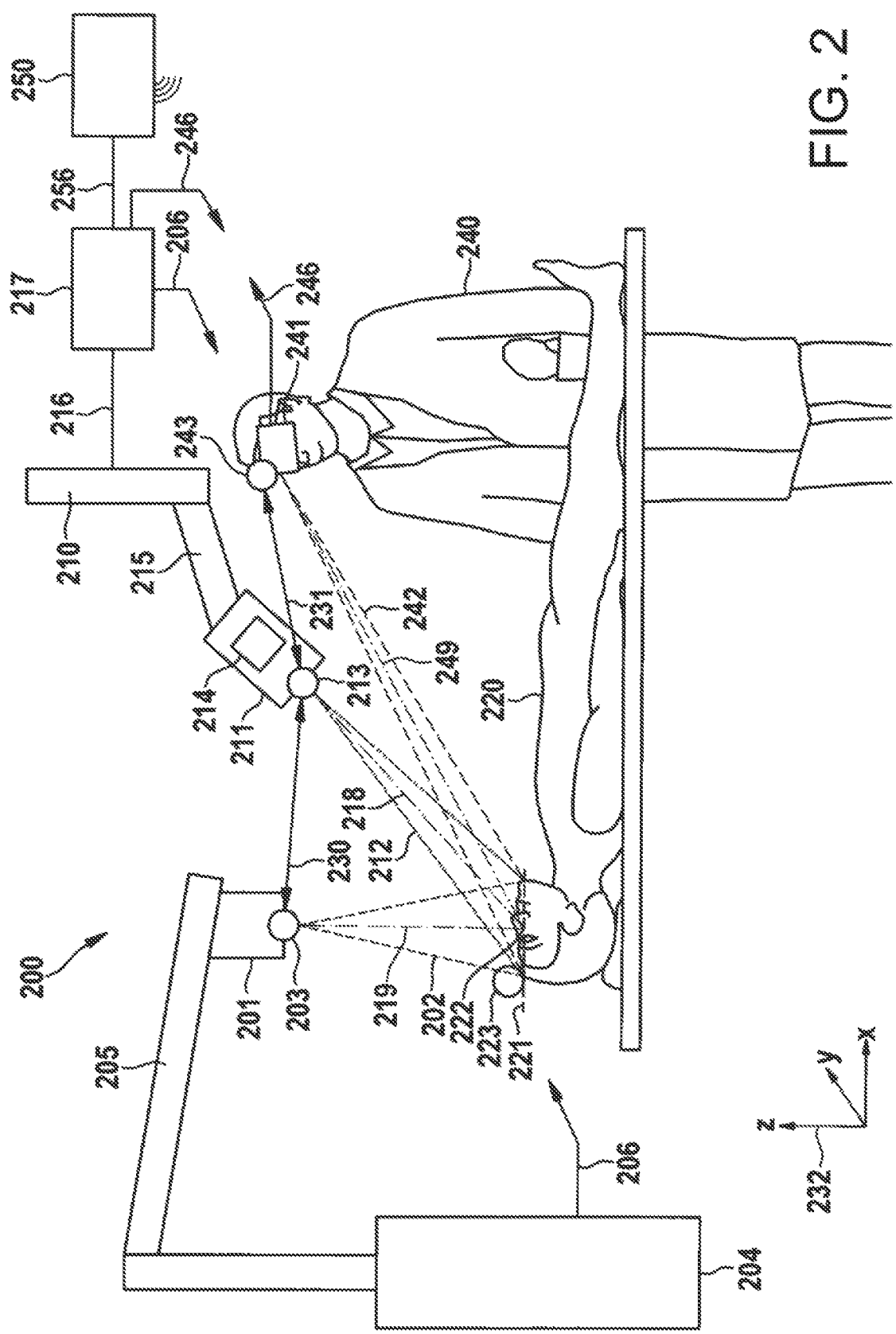
FIG. 2 shows a schematic illustration of a second visualization system.

FIG. 2 shows a schematic illustration of a second visualization system 200.

The second visualization system 200 in accordance with FIG. 2 has the same components as the first visualization system 100 in accordance with FIG. 1, with the reference signs being increased by 100.

The illumination apparatus 200 in accordance with FIG. 2 differs from the illumination apparatus 100 in accordance with FIG. 1 in that additionally an observer 240 having a head-borne second image capturing apparatus 241 observes an object plane 221 of the surgical region. A second observation beam path 242 having a second optical axis 249 is formed between the second image capturing apparatus 241 and the object plane 221.

The head-borne second image capturing apparatus 241 is a head-mounted display, also referred to as a HMD. The HMD comprises a camera or an image sensor and can include one or more additional optical components, which are arranged between the eye of the observer 240 and the object plane 221. The HMD comprises a display, which is arranged in front of the eyes and presents an image of the object region which has been recorded by the camera or the image sensor. The image can be presented with a magnification factor or without magnification. The magnification factor can be low and can for example be less than two. In the HMD, the camera and the display are rigidly coupled.

The second image capturing apparatus 241 is coupled to a control apparatus 217 via a fourth connection 246. The fourth connection 246 can be embodied with a cable, but is typically set up without cables. The connection without cables can be embodied for example via infrared, radio, Bluetooth or WLAN. The transmission of images of the second image capturing apparatus 241 to a display apparatus is possible. In one exemplary embodiment, the display arranged in the second image capturing apparatus 241 can also display images of those images which have been captured in a first image capturing apparatus 201.

Arranged on the second image capturing apparatus 241 is a fourth reference element 243. The fourth reference element 243 permits the determination of a position and orientation of the second image capturing apparatus 241 in space by a pose capturing unit 250.

If a position and orientation of the fourth reference element 243 have been ascertained by the pose capturing unit 250, the control unit 217 can calculate from these data a fourth reference point for the fourth reference element 243. Between the second reference point, which has been ascertained by the second reference element 213, which is arranged on an illumination apparatus 211, and the fourth reference point, the distance and the relative position between the second image capturing apparatus 241 and the illumination apparatus 211 can be calculated.

The control unit 217 can calculate from these data, together with the further data which have been ascertained by the pose capturing unit 250, the position and orientation of the first image capturing apparatus 201, the object plane 221 in the tissue region, the second image capturing apparatus 241 and the illumination apparatus 211. An actuator 214 is actuable by the control apparatus 217 in dependence on said data such that at least one property of the illumination apparatus 211 is settable, in dependence on said data, such that the object region having the object plane 221 is illuminated by the illumination apparatus 211.

For this purpose, the actuator 214 can comprise a drive unit for converting the control signals into a mechanical movement. The actuator 214 can set the position and/or the illumination angle in one, two or three axes and set the illumination beam path 212 to the object plane 221 and consequently to the object region.

In a further exemplary embodiment, an optical or electrical property of the illumination apparatus 211 can be set by the actuator 214, for example the illumination spot size, a zoom setting, the light intensity, the illumination focus or the wavelength range.

The illuminated object region can be, in dependence on the properties of the visualization system 200 which are settable by an observer, the object region which is observed by the first image capturing apparatus 201 and/or the object region which is observed by the second image capturing apparatus 201. The illumination of a partial region, for example an intersection, of the object region which is observed by the first image capturing apparatus 201 and of the object region which is observed by the second image capturing apparatus 201 is also conceivable.

In one exemplary embodiment, a third reference element 223 can additionally be arranged on the object 120 that is to be observed. The third reference element 223 permits the determination of a position and orientation of an object 220 to be observed in space.

It is also conceivable for further observers (not illustrated) to observe the object region having the object plane 221 with a further image capturing apparatus.

In another exemplary embodiment, it is also possible for only one or more head-borne image capturing apparatuses, for example HMDs, to be used, in which case the first image capturing apparatus 201 is omitted.

Figure 3:
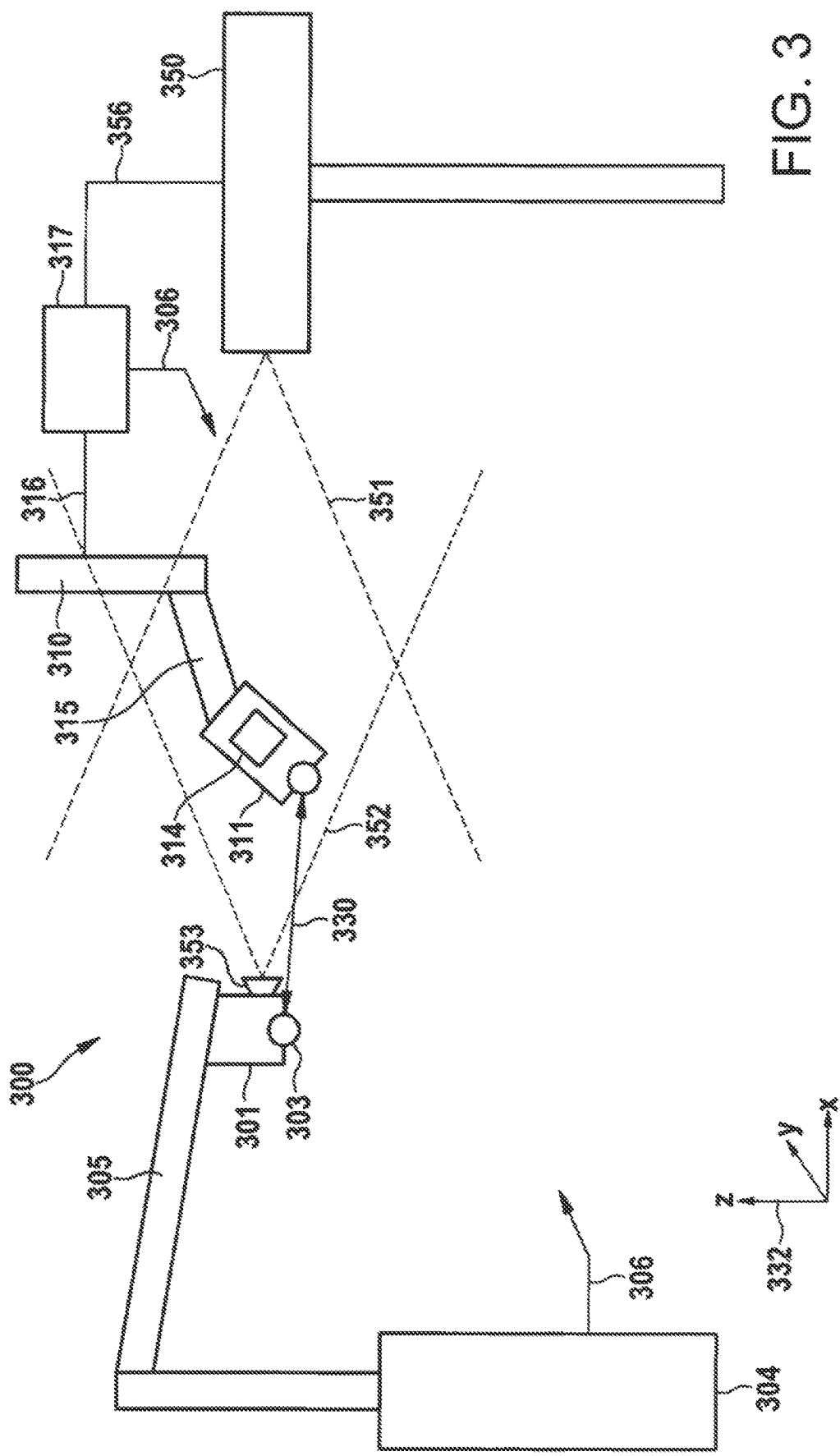
FIG. 3 shows a schematic illustration of a third visualization system having a pose capturing unit.

FIG. 3 shows a schematic illustration of a third visualization system having a pose capturing unit.

A third visualization system 300 in accordance with FIG. 3 has the same components as the first visualization system 100 in accordance with FIG. 1, with the reference signs being increased by 200.

The illumination apparatus 300 exhibits a pose capturing unit 350, which is embodied as a tracking unit. The tracking unit can capture a position and orientation of a first image capturing apparatus 301, of an illumination apparatus 311 and of possible further apparatuses and objects that are not illustrated in FIG. 3. Said objects can be further image capturing apparatuses, for example HMDs, further illumination apparatuses and/or the object that is to be examined. A tracking unit is embodied to capture in each case the position and orientation in terms of space. A tracking ray 351 is schematically illustrated. The capturing is performed at different points in time or in a scanning fashion, with the result that it is possible to track changes over time.

The tracking unit ascertains for each tracking element or each reference point the relative position, i.e., a translation in the x-direction, the x-direction, and the z-direction, and the orientation, i.e., a rotation about the x-axis, the y-axis, and the z-axis, referred to an orthogonal coordinate system 332. The position and orientation can for example also be ascertained relative to a fixed reference point specified by the tracking unit. The tracking method used by the tracking unit can here be based on markers or without markers. A reference element can form a marker, for example. The tracking method can operate on the basis of white light, visible light, or infrared light. Electromagnetic tracking is also conceivable. Alternatively, camera-based tracking solutions are also possible.

In another exemplary embodiment, a pose capturing unit can be formed by a camera 353, which is arranged on the image capturing apparatus 301. An observation region 352 of the camera 353 is illustrated schematically. The images which have been captured by the camera 353 can be processed in a control unit 317, for example in order to ascertain a position and orientation of an illumination apparatus 311. The camera can alternatively also be arranged on the illumination apparatus 311. It is conceivable for further cameras (not illustrated) also to be arranged on the third visualization system 300. A camera 353 can also be configured to capture further apparatuses or objects in space, with the result that the position and orientation thereof in space are also ascertainable by the control unit 317. A pose capturing by a camera 353 can also be combined with one of the above-mentioned tracking systems.

The term "comprising" (and its grammatical variations) as used herein is used in the inclusive meaning of "having" or "including" and not in the exclusive sense of "consisting only of." The terms "a" and "the" as used herein are understood to encompass the plural as well as the singular.

It is understood that the foregoing description is that of the exemplary embodiments of the invention and that various changes and modifications may be made thereto without departing from the spirit and scope of the invention as defined in the appended claims.

LIST OF REFERENCE NUMERALS 100 first visualization system
101, 201, 301 first image capturing apparatus
102, 202, 402 first observation beam path
103, 203, 303 first reference element
104, 204, 304 observation unit
105, 205, 305 first holding arm
106, 206, 306 first connection
110, 210, 310 illumination unit
111, 211, 311 illumination apparatus
112, 212, 412 illumination beam path
113, 213, 313 second reference element
114, 214, 314 actuator
115, 215, 315 second holding arm
116, 216, 316 second connection
117, 217, 317 control unit
118, 218 optical axis of the illumination beam path
119, 219 first optical axis of the first observation beam path
120, 220 object to be observed
121, 221 object plane
122, 222 third reference point
123, 223 third reference element
130, 230, 330 first relative pose
132, 232, 332 coordinate system
150, 250, 350 pose capturing unit
156, 256, 356 third connection
200 second visualization system
231 second relative pose
240 observer
241 second image capturing apparatus
242 second observation beam path
243 fourth reference element
246 fourth connection
249 second optical axis of the second observation beam path
300 third visualization system
351 tracking ray
352 observation region
353 camera

What is claimed is:

1. A visualization system comprising:
    an image capturing apparatus configured to observe an object region having an object plane;
    an illumination apparatus mechanically decoupled from the image capturing apparatus and having an actuator configured to control at least one property of the illumination apparatus;
    a control unit connected to the actuator;
    a pose capturing processor connected to the control unit and configured to determine a relative pose between the illumination apparatus and the image capturing apparatus,
    wherein the actuator is actuable by the control unit in dependence on the relative pose determined by the pose capturing processor to permit the at least one property of the illumination apparatus to be settable to permit the object region having the object plane to be illuminated by the illumination apparatus.

2. The visualization system according to claim 1, wherein the pose capturing processor is configured to permit the relative pose between the image capturing apparatus and the object plane to be ascertainable.

3. The visualization system according to claim 1, wherein a property of the illumination apparatus is an orientation of the illumination apparatus toward the object plane of the object region.

4. The visualization system according to claim 1, wherein a property of the illumination apparatus is formed from an illumination spot size, an intensity, a focus, a zoom, referred to the object plane.

5. The visualization system according to claim 1, wherein the actuator is a robotic apparatus.

6. The visualization system according to claim 1, wherein the relative pose is ascertainable by evaluation of image data recorded by the image capturing apparatus.

7. The visualization system according to claim 1, wherein the pose capturing processor comprises a tracking system.

8. The visualization system according to claim 7, wherein a position and an orientation of the object region having the object plane are ascertainable by the tracking system.

9. The visualization system according to claim 1, wherein a light source of the illumination apparatus is controllable in dependence on data ascertained by the pose capturing processor.

10. The visualization system according to claim 1, comprising at least one further image capturing apparatus.

11. The visualization system according to claim 1, comprising at least one additional illumination apparatus having an additional actuator being actuable by the control unit.

* * * * *